United States Patent
Bandini et al.

(10) Patent No.: US 12,398,358 B2
(45) Date of Patent: Aug. 26, 2025

(54) THREE-DIMENSIONAL (3D) TISSUE SCAFFOLD WITH CELL ALIGNMENT

(71) Applicant: The Trustees of Princeton University, Princeton, NJ (US)

(72) Inventors: Stephen B. Bandini, Newton, MA (US); Joshua Spechler, Cherry Hill, NJ (US); Craig Arnold, Princeton, NJ (US); Jeffrey Schwartz, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 246 days.

(21) Appl. No.: 15/992,272

(22) Filed: May 30, 2018

(65) Prior Publication Data

US 2018/0346862 A1 Dec. 6, 2018

Related U.S. Application Data

(60) Provisional application No. 62/512,257, filed on May 30, 2017.

(51) Int. Cl.
 *C12M 1/12* (2006.01)
 *A61L 27/18* (2006.01)
 (Continued)

(52) U.S. Cl.
 CPC ............ *C12M 25/14* (2013.01); *A61L 27/18* (2013.01); *A61L 27/3804* (2013.01);
 (Continued)

(58) Field of Classification Search
 CPC .................. C12N 2535/00; C12N 2535/10
 See application file for complete search history.

(56) References Cited

U.S. PATENT DOCUMENTS

| 8,796,015 | B2 * | 8/2014 | Gingras | A61L 27/16 |
| | | | | 435/395 |
| 2011/0160869 | A1 * | 6/2011 | Duch | C12M 25/00 |
| | | | | 623/23.5 |

(Continued)

FOREIGN PATENT DOCUMENTS

| WO | WO 2010/008905 A3 | * | 1/2011 | ............... A61F 2/02 |
| WO | WO 2016/118349 | * | 7/2016 | ............... B05D 1/32 |

OTHER PUBLICATIONS

Mata et al. ("A three-dimensional scaffold with precise micro-architecture and surface micro-textures," Biomaterials, vol. 30, Issue 27, Sep. 2009, pp. 4610-4617) (Year: 2009).*

(Continued)

*Primary Examiner* — Frank J Vineis
*Assistant Examiner* — Nicole T Gugliotta
(74) *Attorney, Agent, or Firm* — FOX ROTHSCHILD LLP

(57) ABSTRACT

Polymeric substrates, optionally in sheet form, treated with a thin layer of photoresist are perforated by laser ablation. Following removal of the photoresist the polymer substrates perforated with holes are patterned in stripes by photolithography, which is followed by synthesis of a cell-adhesive organometallic/self-assembled monolayer of phosphonate (SAMP) interface in the exposed regions, providing well-aligned continuous stripes for various levels of perforation. Cells plated on each of these 2-dimensional (2D) perforated surfaces attach to the interface and spread in alignment with pattern fidelity that is as high as that measured on a non-perforated, patterned substrate. A stack of such 2D patterned polymers yields a 3-dimensional (3D) device which facilitates cell growth and viability via the perforations.

21 Claims, 3 Drawing Sheets

(51) Int. Cl.
*A61L 27/38* (2006.01)
*C12M 1/26* (2006.01)
*C12N 5/00* (2006.01)
*A61F 2/00* (2006.01)

(52) U.S. Cl.
CPC ........... C12M 33/00 (2013.01); C12N 5/0068 (2013.01); *A61F 2002/0086* (2013.01); *A61L 27/3891* (2013.01); *A61L 2400/18* (2013.01); *C12N 2533/40* (2013.01); *C12N 2535/00* (2013.01); *C12N 2535/10* (2013.01)

(56) References Cited

U.S. PATENT DOCUMENTS

2014/0243995 A1* 8/2014 Kolewe ............... A61L 27/3804
623/23.72

2014/0330392 A1* 11/2014 Schwartz ............... C12M 25/14
435/402
2018/0282678 A1* 10/2018 Castillo .................. C12M 23/28

OTHER PUBLICATIONS

Millapore Sigma, "Poor Cell Growth Troubleshooting" : https://www.sigmaaldrich.com/US/en/technical-documents/technical-article/cell-culture-and-cell-culture-analysis/mammalian-cell-culture/poor-cell-growth (Year: 2021).*

Bandini, et al: "Perforation Does Not Compromise Patterned Two-Dimensional Substrates for Cell Attachment and Aligned Spreading", ACS Biomater. Sci. Eng. 2017, 3, 3123-3127.

Bityurin, et al: "Models for Laser Ablation of Polymers", Chem. Rev. 2003, 103, 519-552.

Thomas Lippert: "Laser Application of Polymers", Adv Polym Sci, 2004, 168, 51-246.

* cited by examiner

THREE-DIMENSIONAL (3D) TISSUE SCAFFOLD WITH CELL ALIGNMENT

CROSS-REFERENCE TO RELATED APPLICATIONS

This application claims the benefit under 35 USC § 119(e) of U.S. Provisional Application No. 62/512,257 filed on May 30, 2017, the entire disclosure of which is incorporated herein by reference.

STATEMENT REGARDING FEDERALLY SPONSORED RESEARCH OR DEVELOPMENT

This invention was made with government support under Grant No. DMR-0819860 and Grant No. DMR-1420541 awarded by the National Science Foundation. The government has certain rights in the invention.

FIELD OF THE INVENTION

The present invention is related to the field of three-dimensional tissue scaffolds capable of supporting cell alignment and growth, suitable for various medical applications.

BACKGROUND

A challenge for tissue engineering is to direct cell organization throughout a three-dimensional (3D) space in a 3D device. Ideally such a device should induce cells to adopt the specific, native-like organization characteristic of a particular tissue type that is required for its proper function. Among such scaffold models are 3D printed structures, hydrogels, porous foams, and exogenous extracellular matrices (ECMs). These scaffold classes have been constructed artfully using synthetic or natural materials to incorporate, for example, growth factors, or cell-attachment peptides to improve bioactivity. Other 3D scaffolds have been designed to incorporate microfluidic channels to mimic vascularization. Several of these have shown clinical promise for tissue repair. Tissue repair, however, is often marked by scar tissue formation, characterized by the loss of the native organization of the ECM and, consequently, loss of function.

SUMMARY OF THE INVENTION

Templating spatially aligned cell growth in a 3D construct that leads to a similarly aligned ECM provides the basis for a scaffold model to recapitulate native tissue properties. 3D scaffold constructs can be envisaged as a stack of two-dimensional (2D) patterned sheets, similar to 3D printing which occurs effectively through layer-by-layer 2D printing. However, such stacks of 2D sheets need to be characterized by spatially controlled cell spreading on the surfaces of the 2D sheets in order provide a viable layered or stacked 3D device.

The disclosed method to accomplish aligned cell spreading and ECM assembly has been demonstrated on a range of biomaterial polymers. In some aspects the method involves patterning with a cell-adhesive, two-component interface consisting of micron-dimensioned continuous stripes of an organometallic layer, preferably a zirconium or titanium oxide, alkoxide, or mixed oxide/alkoxide, that is terminated with a self-assembled monolayer of a cell-adhesive phosphonate (SAMP), preferably an α,ω-diphosphonate. This nanometer-thin construct actively templates attachment and proliferation of plated cells in register with the chemical pattern; cell proliferation is unconstrained in the linear direction and remains aligned over the entire surface, and cell-assembled ECM is also in register with the organometallic/phosphonate adduct pattern. Stacking such sheets in a 3D construct could, however, be unfavorable for cell viability in the depths of the device, i.e., multiple layers down. This is because lateral transport of oxygen and nutrients from the device periphery to growing cells toward the device's center, and removal of waste products from the center of the device, could be limiting. If perforations or holes were to be present in each 2D-patterned layer of a 3D construct, transport of nutrients and waste products throughout the device would be facilitated; yet such holes could compromise cell templating. The present disclosure demonstrates that polymer films (e.g., polyetherether ketone (PEEK)) can be perforated systematically to at least 20% to about 30% of their nominal surface areas, and that such perforations do not compromise controlled patterning with a cell-adhesive organometallic/phosphonate adduct interface. Furthermore, it is demonstrated herein that these surfaces have the ability to template cell spreading with spatial alignment control as strong as that achieved using non-perforated surfaces.

Thus, one aspect of the invention is directed to a coated 2D construct that supports cell attachment and alignment across two dimensions, comprising a) a biocompatible polymer substrate, in a form such as a sheet, comprising a pattern of holes therethrough extending across the two dimensional surface of the substrate; and b) a patterned layer of an organometallic/-phosphonate adduct coated on the surface of the substrate, the organometallic/phosphonate adduct comprising a self-assembled monolayer of a cell-adhesive phosphonate (SAMP) ligand. The polymer of the biocompatible polymer substrate or sheet can comprise polyetherether ketone (PEEK). The cell-adhesive SAMP layer can be patterned in continuous parallel lines. The holes of the construct can comprise up to about 30% of the nominal surface area of the polymer substrate. The holes of the construct can be introduced, for example, by laser ablation after first applying a photoresist-coating to the polymer substrate, where the photoresist is removed after ablation. The organometallic/phosphonate adduct of the construct can comprise a metal alkoxide, a metal oxide, or a metal mixed oxide-alkoxide. The metal can be zirconium or titanium. For example, the organometallic/phosphonate adduct can comprise zirconium tetra(tert-butoxide). Preferably the SAMP of the coated construct comprises a phosphonic acid covalently attached to the organometallic interface to form an organometallic/phosphonate adduct, where the phosphonic acid contains functionality adapted for cell binding. The cell-binding phosphonic acid can comprise one or more functional groups selected from polyol moieties, sugar alcohol moieties, hydroxyl functional groups, amino functional groups, carboxylic acid functional groups, carboxylate ester functional groups, phosphonic acid functional groups, phosphonate functional groups, ether functional groups, alkyne functional groups, azide functional groups and thiol functional groups. Preferably the phosphonic acid is a diphosphonic acid, more preferably an α,ω-diphosphonic acid. The α,ω-diphosphonic acid is preferably a $C_3$-$C_{16}$ α,ω-diphosphonic acid, and can be, for example, 1,4-butanediphosphonic acid or 1,12-dodecanediphosphonic acid.

The 2D construct can further comprise cells attached to the coated surface of the polymer substrate. The cells preferably assemble an extracellular matrix (ECM) aligned with the SAMP pattern. For example, the cells can comprise NIH 3T3 fibroblasts, or other suitable cells that form an ECM.

Another aspect of the invention is directed to a 3-dimensional (3D) construct which supports cell attachment and alignment, comprising stacked layers of the above-described 2D construct. The attached cells can comprise NIH 3T3 fibroblasts, or other suitable cells that form an ECM.

Yet another aspect of the invention is directed to a method of preparing a 2D construct which supports cell attachment and alignment across two dimensions, comprising the steps of a) providing a biocompatible polymer substrate, for example in the form of a sheet; b) coating the polymer substrate with photoresist to produce a photoresist-protected polymer substrate; c) forming a pattern of holes through the photoresist-protected substrate to produce a perforated protected substrate; d) removing the photoresist from the perforated protected substrate to produce a perforated polymer substrate; e) patterning the perforated substrate with a striped photoresist coating pattern to produce a perforated polymer substrate having a photoresist stripe-protected surface; f) forming a coating of a cell-adhesive organometallic/phosphonate adduct on the stripe-protected surface of the perforated polymer substrate; and g) removing the photoresist from the polymer substrate to form a construct coated with organometallic/phosphonate adduct stripes, where the construct supports cell attachment and alignment across two dimensions. Regarding the method of preparing a construct, the polymer of the biocompatible polymer substrate can comprise polyetherether ketone (PEEK). Regarding the method of preparing a construct, the holes or perforations can be introduced by laser ablation. Regarding step f), the cell-adhesive organometallic/phosphonate adduct is formed on the polymer substrate surface which is not protected by the stripes of photoresist.

Still another aspect of the invention is directed to a method of preparing a 2D construct comprising an aligned ECM, comprising the step of incubating the above-described 2D construct with cells. The cells can be, for example, NIH 3T3 fibroblasts, or other suitable cells that form an ECM.

A further aspect of the invention is directed to a method of preparing a 3D construct which supports cell attachment and alignment, comprising the steps of a) incubating multiple of the above-described 2D constructs with cells to provide cell-attached constructs; and b) stacking the multiple cell-attached constructs into a 3D construct. The cells can be, for example, NIH 3T3 fibroblasts, or other suitable cells that form an ECM.

BRIEF DESCRIPTION OF THE DRAWINGS

(FIG. 1A) Perforations were introduced by laser ablation without a photoresist cover layer on a polymer film; after sonication in ethanol, a large debris field remained around the ablated hole; (FIG. 1B) with photoresist protection, debris landed on the photoresist layer, and sonication in ethanol to remove photoresist yielded a well-defined hole with minimal debris surrounding it. Optical images; scale bar=40 µm.

(FIG. 2B) 10% coverage via "head-to-tail" ablation; (FIG. 2C) 10% coverage by "side-to-side" ablation; and, (FIG. 2D) 20% coverage. Each surface was functionalized with the $ZrO_2$-phosphonate interface patterned in 30 µm×30 µm stripes; scale bar=100 µm. A SEM image showed well defined patterning around the laser-ablated perforation (FIG. 2E), and the Energy-dispersive X-ray spectroscopy (EDX) map of $Zr_{L\alpha 1}$ (FIG. 2F) confirmed that the $ZrO_2$-phosphonate modification conforms to the pattern.

(FIG. 3A) non-perforated PEEK; (FIG. 3B) 5% nominal surface coverage by holes; (FIG. 3C) 10% coverage via the "head-to-tail" ablation scheme or (FIG. 3D) by the "side-to-side" ablation scheme; (FIG. 3E) 20% coverage. Magnification 10×, scale bar=100 µm. (Bottom row): Representative Fast Fourier Transform (FFT) outputs of actin images for each of the surfaces depicted immediately above (FIGS. 3A-E). FFT outputs are shown with lines though each oval to measure the aspect ratio, which is indicated at the bottom as an average ±1 standard deviation; the lower the number, the better the alignment.

DETAILED DESCRIPTION OF PREFERRED EMBODIMENTS

Definitions

Figure 1A:
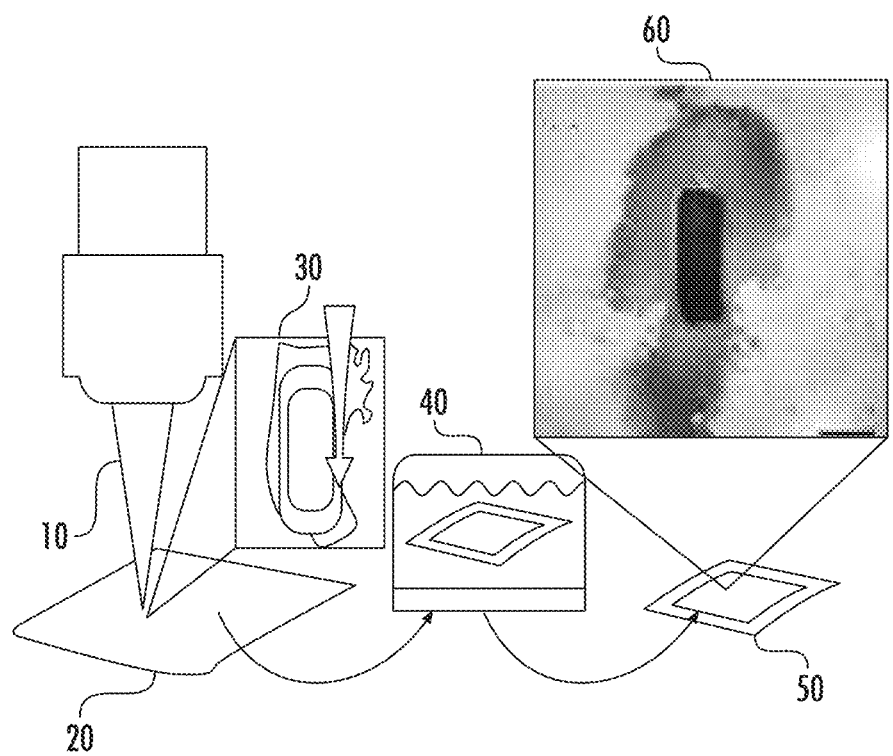
FIGS. 1A and 1B show the protection scheme for laser ablation of polymer films.

As defined herein the term "stripe" refers to a continuous linear coating, for example of photoresist, organometallic oxide or organometallic/phosphonate, having specified width, across the polymer surface of the substrate. The stripes typically are continuous and parallel. The stripes are deposed continuously across the polymer surface, and each stripe layer consists entirely of either the photoresist, organometallic oxide or organometallic phosphonate layer. As a result of the parallel patterning of the coating, the underlying polymer base layer surface also occurs as continuous linear stripes between the coating stripes, having a specified width (which is equivalent to the separation between the coating stripes). The dimensions of the photolithographic patterns can be, for example, (width of stripe X space between stripes; all nominal dimensions are in µm): 10×10, 20×20, 10×20, 20×10, 20×30, 30×10, 30×30, 40×30, 50×30, 60×30, and 100×40. Such continuous stripes on a patterned substrate allow for cell spreading unconstrained within the continuous stripes in the linear dimension. In contrast, for a row of discrete boxes or dots, the cells are constrained within the shape of the box or dot, thereby precluding cell spreading in a line without constraint.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention. The term "about" generally refers to plus or minus 10% of the indicated number. For example, "about 10%" may indicate a range of 9% to 11%, and "about 20" may mean from 18 to 22. Other meanings of "about" may be apparent from the context, such as rounding off, so, for example "about 1" may also mean from 0.5 to 1.4.

EMBODIMENTS

As disclosed herein, polymeric substrates, such as those in sheet-form, can be perforated by ablation or another method that provides holes through the substrate, where the holes are approximately cell-sized or slightly larger, e.g. about 20-40 microns, up to about 130 microns, and are uncompromised by a debris field when the substrates are first treated with a thin protective layer of photoresist. Preferably the ablation is laser ablation, which cleanly provides holes of controlled size. Polymer substrates, e.g. sheets, perforated with holes comprising 5%, 10%, 20% up to about 30% of the nominal surface area are then patterned in stripes by photolithography, which is followed by synthesis in exposed regions of a cell-adhesive organometallic/α,ω-diphosphonate adduct interface. Preferably the α,ω-diphosphonate is a $C_3$-$C_{16}$ α,ω-diphosphonate, more preferably 1,4-butanediphosphonic acid or 1,2-dodecanediphosphonic acid. Microscopic and SEM analyses following removal of unexposed photoresist show well-aligned stripes for all levels of these perforations, with respect to the percentage of nominal surface area removed. Cells, such as NIH 3T3 fibroblasts, plated on each of these 2D perforated surfaces, attach to the interface and spread in alignment with pattern fidelity in every case that is as high as that measured on a corresponding non-perforated, patterned substrate. A stack of such 2D patterned polymers yields a 3-dimensional (3D) device which facilitates cell growth and viability via the perforations.

Figure 1B:
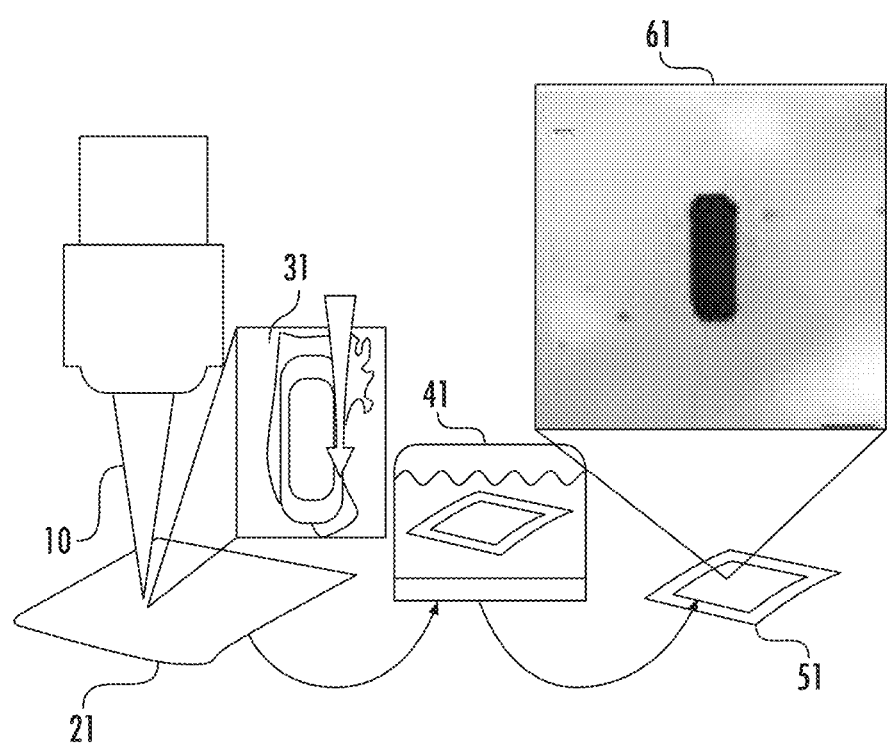

Referring to FIG. 1A, a laser 10 is employed to ablate holes through a polymeric substrate 20 which is not pre-coated with a protective layer of photoresist. The ablation produces holes 30 and ablation debris that falls on the substrate. Subsequent solvent bath treatment 40 of the ablated substrate with, for example ethanol, provides the washed substrate with holes therethrough 50. However, a debris field 60 remains surrounding the holes as a result of the laser ablation process, which debris is not washed off by the bath treatment 40. In contrast, FIG. 1B shows the same process for a photoresist-coated polymeric substrate 21. The laser 10 ablates holes through protected substrate 21 producing holes 31, with ablation debris falling on the protective photoresist coating. Solvent bath treatment 41 of the ablated protected substrate, for example with ethanol, removes the protective photoresist coating and the ablation debris, providing a cleaned substrate with holes therethrough 51, which shows no ablation debris surrounding the holes 61.

In a typical experiment, a 355 nm diode-pumped, solid state-pulsed Nd:$YVO_4$ laser was used to perforate 50 μm thick PEEK films. The laser beam was focused to a diameter ca. 8 μm at an energy ca. 40 μJ, yielding a fluence of ca. 80 J/$cm^2$, which is in accord with published values for the ablation threshold and hole depth for PEEK films ablated by a 308 nm XeCl excimer pulsed laser; which was adequate to cut through the PEEK film in a single pass. The laser pulsed every 1 μm while tracing out the perforations, and the stages moved at a speed of 10 mm/s, giving a laser repetition rate of 10 kHz. Initial attempts at ablating clean 1 cm×1 cm PEEK substrates showed that the perforation process yielded a debris field which could be visualized by optical microscopy as large, dark areas surrounding the ablated holes (FIG. 1A 60); sonication in ethanol did not remove the debris. This problem was obviated through the expedient of first coating the polymer coupons with the same photoresist that was used subsequently for surface photolithographic patterning (FIG. 1B). Thus, when photoresist AZ-5214E was spin cast on both sides of the PEEK coupons and then heated to cure (95° C.), debris from the ablation procedure landed on top of the photoresist layer; removal of the photoresist by sonication in ethanol then showed the formation of well-defined perforations that were surrounded by clean polymer (FIG. 1B 61).

Figures 2A, 2B, 2C, 2D, 2E, 2F:
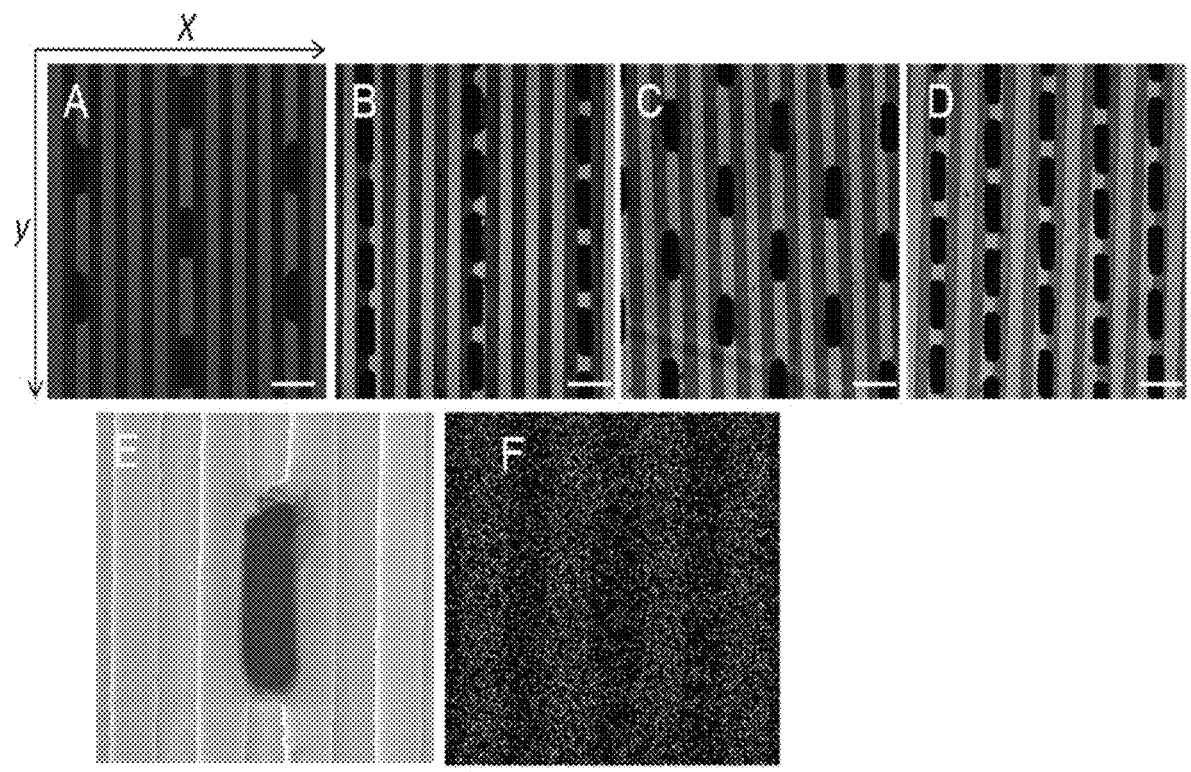
FIGS. 2A, 2B, 2C, 2D, 2E and 2F show optical images of perforated PEEK substrates with (FIG. 2A) 5% surface coverage by holes.

Perforations of 130 μm×30 μm were chosen to be large enough to prevent blockage of the hole by a single cell. Perforations on PEEK surfaces were introduced in several patterns such that the distance from an attached cell to any hole would be no more than 200 μm, the estimated maximum distance that oxygen diffuses from a capillary to support metabolically active tissue. Substrates where prepared in which 5%, 10% and 20% of their nominal surface areas consisted of holes in order to test the limits of the patterning procedures. Doubling the number of holes to convert 5% nominal surface coverage (FIG. 2B) to 10% was done in either a "head to tail" (FIG. 2B) or a "side to side" (FIG. 2C) configuration; surfaces with 20% nominal hole coverage were created by doubling these numbers of ablations (FIG. 2D). Photolithography by spin-coating photoresist onto heavily perforated surfaces has not been previously disclosed in the art, and a minor complication was observed in that the perforated polymer coupon did not attach to the spin coater chuck for deposition of the photoresist, because the holes obviate a vacuum seal between the polymer coupon and the chuck of the spin coater. This was addressed by first adhering the perforated polymer to a glass slide using several drops of uncured photoresist; the PEEK/glass ensemble was then spin-coated with additional photoresist at 4000 rpm for 40 sec, followed by baking at 95° C. for 45 sec. The ensembles were exposed to UV irradiation (365 nm, 4W) through a photomask for 40 sec to create 30 μm wide stripes separated by 30 μm (30 μm×30 μm); in each case patterned stripes of the photomask were oriented parallel to the perforated holes. Treating with AZ-MIF 300 developer for 35 sec gave oriented, striated patterns on the perforated polymer coupon (FIG. 2). The ensembles were then exposed to vapor of zirconium tetra(tert-butoxide) (Zr(O-t-bu)$_4$) for 5 min at $10^{-3}$ torr; oxygen-containing functionalities of the PEEK polymer enable its coordinative bonding to Zr(O-t-bu)$_4$. Heating to 65° C. gave a surface-bound, cross-linked, mixed zirconium oxide/tert-butoxide pattern, which was converted to patterned $ZrO_2$-phosphonate by immersion in a solution of 1,4-butanediphosphonic acid in ethanol (0.25 mg/mL). This ethanol treatment also removed residual photoresist. Optical microscopy showed the patterned regions to be parallel with the ablated holes; both holes and patterns were uniform over the entire PEEK surface, with hole coverage of 5%, 10%, and 20% of the substrates nominal areas (FIGS. 2 A-E). Even when 20% of the surface has been removed by ablation, the substrate could still be spin-coated with an adequate layer of photoresist in both uniformity and thickness for photolithographic patterning. Energy-dispersive X-ray spectroscopy (EDX) analysis (FIG. 2F using $Zr_{L\alpha 1}$) confirmed the composition of these patterns to be the desired $ZrO_2$-phosphonate adduct. A similar EDX analysis was obtained using $P_{K\alpha 1}$ (data not shown).

NIH 3T3 fibroblasts were plated on $ZrO_2$-phosphonate SAMP-patterned PEEK substrates with 5%, 10% and 20% nominal surface hole coverages to determine if perforation adversely affected cell attachment and spreading in alignment with the pattern. Cells were plated at 30,000 cells/cm$^2$ of nominal substrate surface in Dulbecco's modified eagle medium (DMEM) with 10% bovine calf serum, and were grown for 3 days before being fixed with 3.7% formaldehyde in phosphate-buffered saline, permeabilized with NP-40, and stained with rhodamine-phalloidin to visualize actin filaments. Analysis showed that the cells had spread around and between, but not over, the holes, and were in alignment with the $ZrO_2$-phosphonate pattern (FIGS. 3A-E). Actin was found to be aligned over the surfaces in register with the patterns after cells had reached full confluence (FIG. 4).

Figures 3A, 3B, 3C, 3D, 3E:
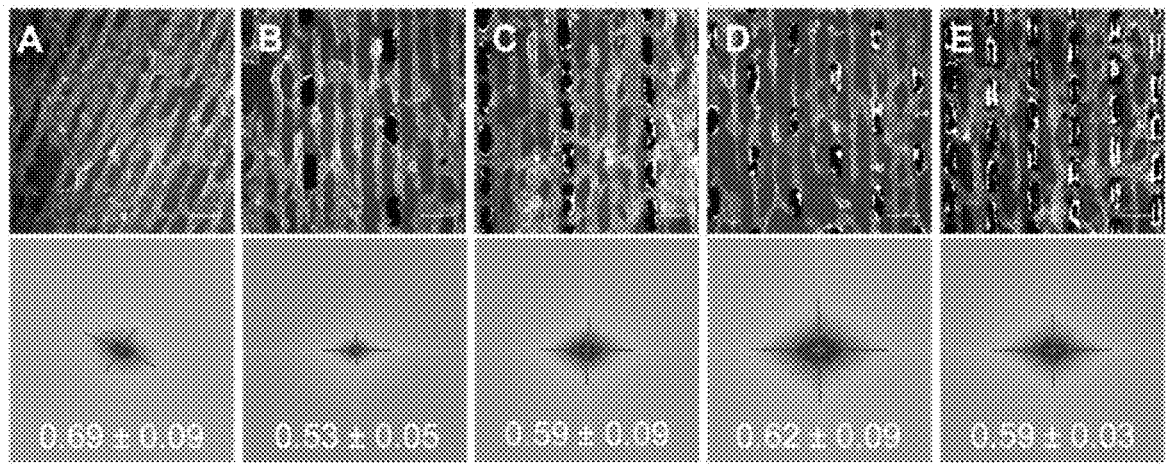
FIGS. 3A, 3B, 3C, 3D and 3E show (Top row): Representative images of actin-stained NIH 3T3 fibroblasts grown on patterns of the $ZrO_2$-phosphonate on perforated PEEK substrates after 3 days.
Figure 4:
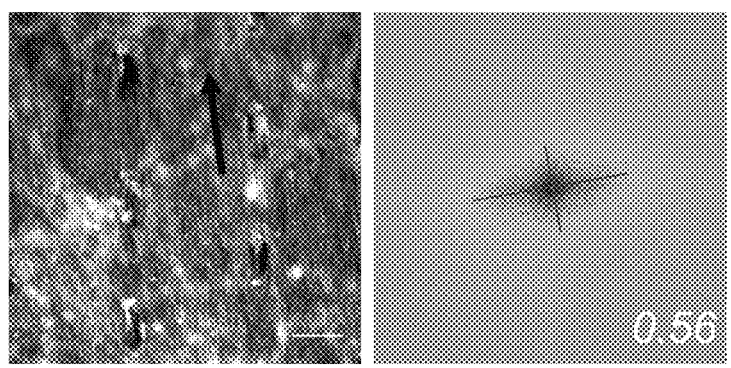
FIG. 4 shows an optical image of a fully confluent layer of cells on a 5% perforated substrate at 7 days (arrow indicates direction of the pattern), and the corresponding FFT output.

Quantitatively comparing cell alignment on patterned, non-perforated versus patterned, perforated surfaces was made by measuring aspect ratios of Fast Fourier Transform (FFT) outputs from stained actin images of adhered cells (FIG. 3). FFT analysis was performed on four 10× images each a perfect square of 1024×1024 pixels. Image contrast was normalized with pixel saturation set at 0.4%; FFT was determined using ImageJ software in which grayscale output was colorized using the "spectrum" table. The aspect ratio is defined as the width of the FFT output oval divided by its length; thus, the smaller the aspect ratio, the better the alignment. This ratio was 0.69±0.09 for cells on patterned, non-perforated PEEK (FIG. 3A); patterned, perforated substrates had ratios of 0.53±0.05, 0.59±0.09, 0.62±0.09, and 0.59±0.03 for cells on surfaces with 5% hole coverage (FIG. 3B), 10% hole coverage via "head-to-tail" ablation (FIG. 3C), 10% hole coverage via "side-to-side" ablation (FIG. 3D), and 20% hole coverage (FIG. 3E), respectively. These data show that the cells are as well-aligned on patterned, perforated PEEK as they are on patterned, non-perforated PEEK, which was further supported by statistical analysis using ANOVA ($\alpha$=0.05), where no statistical difference was found for the aspect ratio among all of the PEEK surfaces (p=0.114). There is no apparent correlation between hole number or alignment with FFT-measured aspect ratios.

Thus the present disclosure demonstrates that clean perforation of a surface-protected polymer film can be accomplished, preferably by laser ablation, and that this material can be patterned to template spatially controlled cell spreading in a way that is as effective as it is on unperforated polymer substrates. Protecting the polymer (e.g., PEEK) with a thin layer of photoresist prior to laser treatment causes all debris from ablation to be deposited on top of this photoresist layer, which is then removed, preferably by sonication in ethanol. Ablation-perforated polymer was easily patterned by photolithography to prepare cell-adhesive organometallic/phosphonate adduct striations. Patterned polymer films are able to template cell spreading in alignment with these striations, even when perforations account for up to 20% to 30% of the nominal surface area. Given the ease of the disclosed methods, the procedures for material transformation provides an effective approach to 3D constructs based on stacks of 2D patterned polymers. Coupled with demonstrated excellence in spatially determined surface chemical modification of polymer films and of ECM assembly on them, these methods are applicable to fabricating tissue scaffolds comprising cell-assembled matrices, or organ-on-a-chip technologies, that effectively recapitulate native tissue architectures. Other possible uses include diagnostic applications and cell-involved electrodes.

One aspect of the invention is directed to a coated construct that supports cell attachment and alignment across two dimensions, comprising a) a biocompatible polymer substrate, optionally in sheet form, comprising a pattern of holes therethrough extending across the two dimensional surface of the substrate; and b) a patterned layer of an organometallic/phosphonate adduct coated on the surface of said substrate, the organometallic/phosphonate adduct comprising a self-assembled monolayer of a cell-adhesive phosphonate (SAMP) ligand. The polymer of the biocompatible polymer substrate can comprise polyetherether ketone (PEEK), optionally in sheet form. The cell-adhesive SAMP layer can be patterned in continuous parallel lines. The holes of the construct can comprise up to about 30% of the nominal surface area of the polymer substrate. The percentage of nominal surface area removed can be about 3% to about 30%, or about 5% to about 25%, or about 10% to about 20%. The holes of the construct can be introduced by laser ablation after first applying a photoresist-coating to the polymer substrate, where the photoresist is removed after ablation. The percentage of nominal surface area removed by laser ablation can be 3%, or 5%, or 10%, or 15%, or 25%, or 30%, or any value falling in the range of 3% to 30%.

With regard to cutting holes or perforations in the biocompatible polymers, laser ablation of suitable polymers is well established. See, for example the reviews by N. Bityurin et al., Chem. Rev., 2003, 103, 519-552, "Models for Laser Ablation of Polymers", and T. Lippert, Adv. Polym. Sci., 2004, 168, 51-246, "Laser Application of Polymers". Thus, in addition to PEEK, suitable polymers for laser ablation include, without limitation, polyesters such as polyethylene terephthalate (PET), polyester carbonates, polyacrylates such as poly(methyl methacrylate) (PMMA), and polyimides such as KAPTON™. Other suitable polymers contain photolabile functional groups such as triazene (—N=N—N—), pentazadiene (—N=N—N(R)—N=N—), or the general chromophore —N=N—X— where X=CO, $SO_2$, O, S, —CH=CH—, —N(R)—N=N—, phosphate, or N(R)(R') groups. Selected suitable polymers include those having the following repeating units:

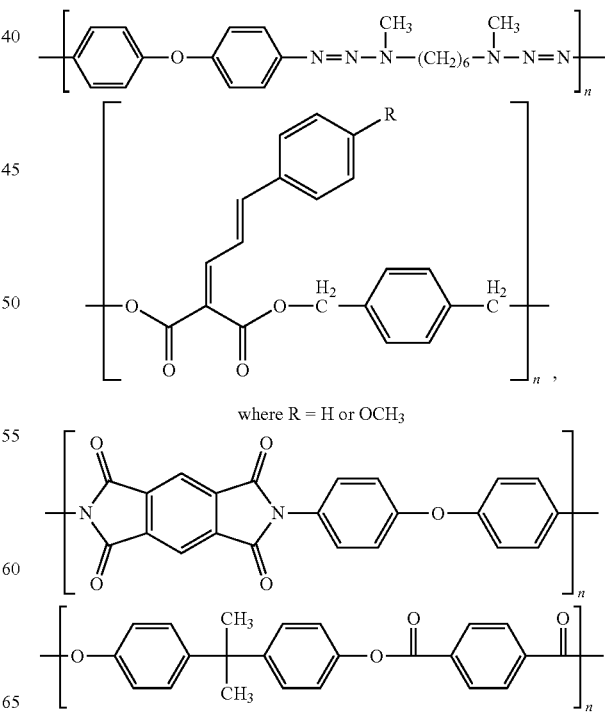

where R = H or OCH$_3$

Such suitable polymers have appropriate absorbance at the irradiation wavelength of the laser. Preferably ablation is at high laser fluence (0.5-10 J cm$^2$).

The organometallic/phosphonate adduct of the construct can comprise a metal alkoxide, a metal oxide, or a metal mixed oxide-alkoxide. The organometallic/phosphonate adduct can comprise a zirconium alkoxide, such as zirconium tetra(tert-butoxide), or can comprise a titanium alkoxide. The metal can be zirconium or titanium. Preferably the SAMP of the coated construct comprises a phosphonic acid covalently attached to the organometallic portion of the organometallic/phosphonate adduct, which phosphonic acid contains functionality adapted for cell binding. The cell-binding phosphonic acid can comprise one or more functional groups selected from polyol moieties, sugar alcohol moieties, hydroxyl functional groups, amino functional groups, carboxylic acid functional groups, carboxylate ester functional groups, phosphonic acid functional groups, phosphonate functional groups, ether functional groups, alkyne functional groups, azide functional groups and thiol functional groups. Preferably the phosphonic acid is a diphosphonic acid, more preferably an α,ω-diphosphonic acid. The α,ω-diphosphonic acid can be a $C_{3-16}$ diphosphonic acid, preferably a $C_{4-12}$ diphosphonic acid, more preferably a $C_4$, $C_6$, $C_8$, $C_{10}$ or $C_{12}$ diphosphonic acid. The α,ω-diphosphonic acid can be 1,4-butanediphosphonic acid, or 1,6-hexanediphosphonic acid, or 1,8-octanediphosphonic acid, or 1,10-decanediphos-phonic acid, or 1,12-dodecanediphosphonic acid, or mixtures of two or more thereof.

The construct can further comprise cells attached to the coated surface of the polymer substrate or sheet. The cells preferably comprise an assembled extracellular matrix (ECM) aligned with the SAMP pattern. The cells can comprise NIH 3T3 fibroblasts, or other suitable cells that form an ECM.

Another aspect of the invention is directed to a 3-dimensional (3D) construct that supports cell attachment and alignment, comprising stacked layers of the above-described construct. The attached cells can comprise NIH 3T3 fibroblasts, or other suitable cells that form an ECM.

Yet another aspect of the invention is directed to a method of preparing a construct which supports cell attachment and alignment across two dimensions, comprising the steps of a) providing a biocompatible polymer substrate, optionally in sheet form; b) coating the polymer substrate with photoresist to produce a photoresist-protected polymer substrate; c) forming a pattern of holes or perforations in the photoresist-protected substrate to produce a perforated protected substrate; d) removing the photoresist from the perforated protected substrate to produce a perforated polymer substrate; e) patterning the perforated substrate with a striped photoresist coating pattern to produce a perforated polymer substrate having a photoresist stripe-coated surface; f) forming a coating of a cell-adhesive organometallic/phosphonate adduct on the stripe-coated surface of the perforated polymer substrate; and g) removing the photoresist from the polymer substrate to form a construct coated with organometallic/phosphonate adduct stripes, where the construct supports cell attachment and alignment across two dimensions. Regarding the method of preparing a construct, the polymer of the biocompatible polymer substrate can comprise polyetherether ketone (PEEK), or other suitable polymer susceptible to hole cutting such as by laser ablation or other method of providing cell-sized holes in a reproducible and controlled size. Regarding the method of preparing a construct, the holes or perforations can be introduced by laser ablation or other method of providing cell-sized holes in a reproducible and controlled size.

Still another aspect of the invention is directed to a method of preparing a construct comprising an aligned ECM, comprising the step of incubating the above-described construct with cells. The cells can be NIH 3T3 fibroblasts, or other suitable cells that form an ECM.

A further aspect of the invention is directed to a method of preparing a 3D construct which supports cell attachment and alignment, comprising the steps of a) incubating multiple constructs (as described above) with cells to provide cell-attached constructs; and b) stacking the multiple cell-attached constructs into a 3D construct. The cells can be NIH 3T3 fibroblasts, or other suitable cells that form an ECM.

In an additional aspect of the invention, the polymer of the biocompatible polymer substrate can react directly with a cell-adhesive phosphonate, such as an α,ω-diphosphonic acid, for example by proton transfer (H$^+$ transfer) or by covalent reaction of the phosphonic acid group. Such polymers may not require an organometallic compound to serve as a bridging layer (to form an organometallic/phosphonate adduct), but such polymers can interact directly with one of the phosphonic acid groups of the α,ω-diphosphonate itself to form an adherent SAMP. Examples of such polymers include appropriately functionalized polyacrylates, polyamides and polyurethanes. Even though these polymers are directly reactive with a phosphonic acid, an organometallic bridging layer can optionally be deposited on such polymers to form an organometallic/phosphonate adduct.

One embodiment of this additional aspect is directed to a coated construct that supports cell attachment and alignment across two dimensions, comprising: a) a biocompatible polymer substrate that is directly reactive with a cell-adhesive phosphonate, comprising a pattern of holes therethrough extending across the two dimensional surface of the substrate; and b) a patterned layer of an α,ω-diphosphonate directly attached to the surface of said substrate in a self-assembled monolayer of cell-adhesive phosphonate (SAMP) ligand in continuous parallel lines; where the directly reactive polymer substrate is selected from the group consisting of polyacrylates, polyamides and polyurethanes.

Another embodiment of this additional aspect is directed to a method of preparing a construct which supports cell attachment and alignment across two dimensions, comprising the steps of: a) providing a biocompatible polymer substrate that is directly reactive with a cell-adhesive phosphonate, optionally in sheet form; b) coating said polymer substrate with photoresist to produce a photoresist-protected polymer substrate; c) forming a pattern of holes through said photoresist-protected substrate to produce a perforated protected substrate; d) removing the photoresist from said perforated protected substrate to produce a perforated polymer substrate; e) patterning said perforated substrate with a striped photoresist coating pattern to produce a perforated polymer substrate having a photoresist stripe-coated surface in continuous parallel lines; f) forming a coating of a cell-adhesive α,ω-diphosphonate directly on the stripe-coated surface of said perforated polymer substrate; and g) removing said photoresist from said perforated polymer substrate to form a construct coated with cell-adhesive α,ω-diphosphonate stripes directly attached to said polymer substrate in continuous parallel lines, wherein said construct supports cell attachment and alignment across two dimensions; and wherein the directly reactive polymer substrate is selected from the group consisting of polyacrylates, polyamides and polyurethanes.

EXAMPLES

General.

Polyetheretherketone (PEEK) film (0.05 mm thickness; Goodfellow Corp.); isopropanol, formaldehyde, 4',6-diamidino-2-phenylindole (DAPI) (Sigma-Aldrich); AZ-5214E photoresist and AZ-300 MIF developer (AZ Electronic Materials); zirconium tetra(tert-butoxide) (Strem Chemicals, Inc.); 1,4-butanediphosphonic acid (Acros Organics); phosphate buffered saline (PBS), rhodamine phalloidin; Hoechst 33258 (Invitrogen); trypsin, versene (LifeTech); Dulbecco's modified eagle medium (DMEM), bovine calf serum (BCS) (Hyclone); nonyl phenoxypolyethoxylethanol (NP-40) (EMD Chemicals); and 200 proof ethanol (Pharmco-Aaper) were used as received. NIH 3T3 fibroblasts were maintained in DMEM supplemented with 10% BCS and passaged 1:10 by volume twice each week. Trypsin was added to versene (1×) before using to lift cells off tissue culture plates.

Example 1. SEM and EDS Analysis

Perforated polymer substrates were characterized with an FEI Quanta 200 Environmental-SEM equipped with an Oxford INCA Synergy 450 energy-dispersive X-ray microanalysis system with an X-Max 80 large area analytical silicon drift detector (SDD) at an acceleration voltage of 5 keV. SEM and EDS were performed in low-vacuum mode (0.53 torr) to avoid melting of the polymer by the electron beam.

Example 2. Preparation of Polymer Films for Laser Ablation

PEEK films were cut into 1 cm×1 cm coupons and cleaned by sonication in ethanol for 15 minutes. Films were rinsed with isopropanol and baked at 95° C. to remove moisture. Both sides of the PEEK films were spin-coated with a layer of AZ-5214E photoresist to protect the native polymer surfaces from debris created during the laser ablation process. The photoresist was cured by heating at 95° C. for 45 seconds.

Example 3. Laser Ablation of Polymer Films

Polymer films were laser ablated with a 355 nm neodymium laser; the laser ablation was automated by a program that fixed the hole size around 30 μm×110 μm and allowed for modification of hole placement on the surface based on the desired hole coverage. After ablation, photoresist and debris were removed by sonication in ethanol for 15 minutes followed by an isopropanol rinse.

Example 4. Photolithography of Perforated Polymer Films

Constructing the patterned interface on perforated PEEK films required modifications to the typical photolithography procedure. Perforated, cleaned PEEK films were baked at 95° C. for 10 minutes prior to photolithography. Due to the presence of the holes, the perforated PEEK films could not be secured to the spin coater with a vacuum; instead, 3 drops of photoresist were deposited and spread on a glass slide to create a surface sticky enough to hold the perforated polymer film during spin-coating. Films were coated with 5 drops of photoresist and spun at 4000 rpm for 40 seconds. The ensemble was then baked at 95° C. for 45 seconds. The photoresist-covered films were exposed to UV radiation through a 30 μm×30 μm photomask for 40 secs. such that the stripes of the photomask were oriented in the same direction as the perforated holes. The films were then developed in AZ-MIF 300 developer for 35 seconds, rinsed vigorously with deionized water, then dried under nitrogen to yield photolithographic patterns.

Example 5. Vapor Phase Deposition of Volatile Organometallic Complex and Formation of $ZrO_2$-SAMP-patterned Perforated Polymer Perforated substrates patterned by photolithography were secured to a glass slide covered with double-sided tape. The tape was patted with a KIMWIPE® Delicate Task Wiper so that it was just sticky enough to interact with the perforated surfaces; ablation increased the fragility of the PEEK so that it would bend upon removal from double-sided tape that was too sticky. The glass slide containing the perforated surfaces was placed inside a deposition chamber equipped with two valves; one was connected to vacuum and the other to a bulb containing zirconium tetra(tert-butoxide). The chamber was evacuated to $1\times10^{-3}$ torr for 10 min. Samples were exposed to vapor of $Zr(O-t-bu)_4$ for 5 min with the chamber opened to vacuum. The bulb and chamber were sealed, the chamber was wrapped with heat tape, and warmed to 65° C. to form a mixed zirconium oxide/alkoxide interface in patterns on the surface of the PEEK. The chamber was then cooled to room temperature and subsequently evacuated to $1\times10^{-3}$ torr for 5 min. After evacuation, the chamber was closed to vacuum and back-filled with zero-grade nitrogen. After closing the valves of both sides of the chamber, the chamber was removed from the vacuum line. The substrates were quickly removed from the chamber and placed in individual vials containing a solution of 1,4-butanediphosphonic acid in ethanol (0.25 mg/mL) for 16 hr to yield polymer films functionalized with patterns on the surface, in which alkoxide ligands were replaced by phosphonate groups. Photoresist was removed from the substrates by sonication in the phosphonic acid-ethanol solution; substrates functionalized with the patterned $ZrO_2$-SAMP interface were then rinsed with isopropanol, dried under nitrogen, and assessed by optical microscopy.

Example 6. Cell Alignment on $ZrO_2$-SAMP-patterned, Perforated Substrates

Cell alignment was assessed using NIH 3T3 fibroblasts. Cells were plated on $ZrO_2$-SAMP-patterned, perforated (for each of the four different hole arrangements) PEEK substrates, and compared versus $ZrO_2$-SAMP-patterned non-perforated PEEK substrates at 30,000 cells/well. Cells were plated on each surface in duplicate. After 3 days, cells were fixed using 3.7% formaldehyde in PBS for 15 min, permeabilized with 0.5% NP-40 (v/v) in PBS for 15 min at room temperature; cell actin was stained with rhodamine-phalloidin (1:40) and cell nuclei were stained with DAPI (1:1000). Antibodies were diluted by volume in PBS containing 2% BSA. Cells were visualized with a Nikon TE2000U fluorescent microscope and images were captured with a QImaging Retiga 1300 camera and iVision software, and were further analyzed using ImageJ software. Fast Fourier transform (FFT) analysis of actin alignment was performed on 10× actin images that were cropped to make a perfect square of 1024×1024 pixels. Image contrast was normalized with pixel saturation set to 0.4%, and the FFT operation was performed by Image J software. The gray scale output was colorized with the "spectrum" table.

Example 7. Evaluating Molecular Diffusion in Stacks of Polymer Films

3T3 Fibroblast cells were plated on seven non-perforated, $ZrO_2$/(4-phosphonobutyl)-phosphonate-covered PEEK control substrates, and on seven perforated, $ZrO_2$/(4-phosphono-butyl)phosphonate-covered PEEK substrates in a 24 well dish, as disclosed above. Cells were plated in DMEM supplemented with 10% BCS at 30,000 cells/well. PEEK films were held down with a Pasteur pipette after 2 hours, when they slowly began to float because of solvent outgassing. After 3 days, the two sets of polymer films ((4-phosphonobutyl)phosphonate-covered, non-perforated, and (4-phosphonobutyl)phosphonate-covered, perforated) were stacked into separate constructs of 7 layers each. An O-ring was placed above the top layer of each stack to hold the layers in place. The well of each stack was filled about half-way by adding 0.75 mL of DMEM supplemented with 10% BCS. 3 hours after stacking, a solution of VITAL HOECHST DYE® was prepared in serum-containing media (40 µg/mL). To the wells containing the stacks, 0.75 mL of the dye-containing media was added very gently, yielding a concentration of VITAL HOECHST DYE® of 20 µg/mL in each well containing the stacks. The dye was allowed to diffuse for 3 hours in the wells; after 3 hours, the polymer films were removed from the stacks layer-by-layer, and each polymer film was placed in a well containing PBS. Cells on each film of each stack were fixed in methanol for 10 minutes, rinsed with PBS 3 times, and then rinsed once with deionized water. Cells were imaged on each film using the UV filter of the Nikon TE2000U fluorescent microscope, and images were captured using QImaging Retiga 1300 camera and iVision. The images captured were carefully noted in relation to their locations on the polymer surfaces.

Example 8. Fluorescence Intensity Quantification

For each cell nuclei image, the maximum and minimum pixel intensity values were determined using the "measure" feature in ImageJ. Eight 200 pixel×200 pixel fields were analyzed for each image; the fields analyzed were located at the edges of the image to minimize the contribution of reflection of the light from the polymer film. The two fields were carefully located on each edge such that they trisected (as closely as possible) each edge. For the perforated surfaces these values were determined in regions that did not contain holes to avoid measuring pixel intensity of hole features. Because each image had a different background value, the minimum value was subtracted from the maximum value to yield an absolute intensity value for each image. The absolute value was then normalized with respect to the background by dividing the absolute value by the minimum value, which then yielded a ratio of fluorescence intensity over background. To derive the plotted relative fluorescence intensity parameter, the ratio of fluorescence intensity over background for each image was divided by the ratio of fluorescence intensity over background for the top layer of its respective stack. Thus the relative fluorescence intensity measurement for the top layer equals 1, by definition. These ratios were then plotted, along with the standard error, to compare relative fluorescence intensity between perforated and non-perforated stacks.

Example 9. Constructing 3D Ensembles of Stacked Patterned, Perforated and Non-Perforated Films 3T3 Fibroblast cells were plated on seven non-perforated, $ZrO_2$—SAMP-patterned PEEK control substrates, and on seven perforated, $ZrO_2$—SAMP-patterned PEEK substrates in a 24 well dish, as disclosed above. Cells were plated in DMEM supplemented with 10% BCS at 30,000 cells/well. PEEK films were held down using a Pasteur pipette after 2 hours at which time they began to float. After 3 days, the two sets of polymer films (patterned/non-perforated, and patterned/perforated) were stacked into separate constructs of seven layers each. Notably, the films were stacked such that the patterns, and consequently the cells, were oriented in alternating directions from layer to layer. An O-ring was placed above the top layer of each stack to hold the layers in place. The media was changed in each well following stacking, and changed once each day for the next 3 days.

Example 10. Visualizing Alignment of Cells in the Stacked Constructs

After 4 days in the stack, the polymer films were removed from the stack, layer by layer, and each polymer film was placed in a well containing PBS. Phase images were taken to compare cell growth on each individual layer before and after stacking using a Nikon Eclipse TS 100 microscope equipped with a Cooke SensiCam camera and iVision software. Cells on each film of the stacks were fixed with 3.7% formaldehyde in PBS, rinsed once with PBS and then permeabilized with NP-40. After rinsing with PBS, the cells were stained with rhodamine phalloidin (1:40) and DAPI (1:1000). Antibodies were diluted by volume in PBS containing 2% BSA. Fluorescence images were taken of the cells on both the non-perforated, patterned films, and the perforated, patterned films. Experimentally, immunofluorescence staining proved to be difficult on the perforated surfaces, most likely because of extra turbulence created by the holes when washing the surfaces with PBS. Phase images taken before immunofluorescence were helpful to corroborate cell density on the surfaces because in some areas cells were washed away by the staining procedure. It was also necessary to submerge perforated surfaces in antibody solution, as opposed to placing a few drops of antibody on the surface, because the solution went through the holes. Fluorescence images were obtained with a Nikon TE2000U fluorescent microscope and images were captured with a QImaging Retiga 1300 camera and iVision software. Images were further analyzed using ImageJ software.

Example 11. Formation of SAMP-Patterned Perforated Polymer without Vapor Phase Deposition of a Volatile Organometallic Complex Perforated substrates are patterned by photolithography and are secured to a glass slide covered with double-sided tape. The tape is patted with a KIMWIPE® Delicate Task Wiper so that it is just sticky enough to interact with the perforated polymer; ablation increases the fragility of the polymer so that it can bend upon removal of double-sided tape that is too sticky. The polymer substrates are quickly placed in vials containing a solution of 1,4-butanediphosphonic acid in ethanol (0.25 mg/mL) for 16 hr to yield polymer films that are phosphonate-functionalized in patterns on the surface; the phosphonates are bonded to the polymer by proton transfer from the phosphonic acid to a basic nitrogen atom of the polymer. Exogenous base such as triethylamine is then added to remove such polymer-bonded protons as soluble ammonium salts that are rinsed away. Any unreacted phosphonic acid in solution is similarly removed as an ammonium phosphonate salt. Photoresist is removed from the polymer by sonication in ethanol; polymer substrates functionalized with the patterned SAMP are then rinsed with isopropanol, dried under nitrogen, and assessed by optical microscopy.

Example 12. Cell Alignment on SAMP-Patterned, Perforated Substrates

Cell alignment is assessed using NIH 3T3 fibroblasts. Cells are plated at 30,000 cells/well on SAMP-patterned, perforated (for each of the four different hole arrangements) polymer substrates, and are compared versus SAMP-patterned, non-perforated polymer substrates. Cells are plated on each surface in duplicate. After 3 days, cells are fixed using 3.7% formaldehyde in PBS for 15 min, permeabilized with 0.5% NP-40 (v/v) in PBS for 15 min at room temperature; cell actin is stained with rhodamine-phalloidin (1:40) and cell nuclei are stained with DAPI (1:1000). Antibodies are diluted by volume in PBS containing 2% BSA. Cells are visualized with a Nikon TE2000U fluorescent microscope; images are captured with a QImaging Retiga 1300 camera and iVision software, and are further analyzed using ImageJ software. Fast Fourier transform (FFT) analysis of actin alignment is performed on 10× actin images that are cropped to make a perfect square of 1024×1024 pixels. Image contrast is normalized with pixel saturation set to 0.4%, and the FFT operation is performed by Image J software. The gray scale output is colorized with the "spectrum" table.

What is claimed is:

1. A 3-dimensional (3D) construct that supports cell attachment and alignment along cell-adhesive continuous parallel stripe patterns, comprising stacked layers of a coated 2-dimensional (2D) construct that supports cell attachment and alignment across two dimensions, each 2D construct comprising:

a biocompatible polymer substrate comprising a laser-ablatable polymer base layer having a pattern of elongated holes therethrough extending across the two-dimensional surface of the substrate, comprising up to about 30% of the nominal surface area of the polymer substrate, wherein each of the elongated holes has a length dimension up to about 130 µm and a width dimension of about 20 to 40 µm; and wherein the elongated holes are arranged in rows such that holes in one row are offset from holes in a neighboring row so that holes in one row are staggered with those in the neighboring row in a direction of row progression, a layer of a cell-adhesive organometallic/phosphonate adduct coating on the surface of said polymer base layer in micron-dimensioned continuous parallel stripes alternating with parallel stripes of the polymer base layer having the holes therebetween;

wherein the phosphonate of said organometallic/phosphonate adduct layer is a self-assembled monolayer of a cell-adhesive phosphonate (SAMP) ligand, wherein said micron-dimensioned parallel stripe-patterned layer is dimensioned to (1) template attachment and proliferation of cells in register with the stripe pattern so that cell proliferation is aligned in the linear stripe direction and remains aligned over the entire surface, and (2) allow the cells to grow to confluence, wherein on each 2D construct, every cell is no more than about 200 µm from at least one elongated hole, and wherein the elongated holes elongate in an orientation parallel to the cell-adhesive stripes.

2. The construct of claim 1, wherein the polymer of said biocompatible polymer substrate is polyetherether ketone (PEEK).

3. The construct of claim 1, wherein said polymer substrate is in sheet form.

4. The construct of claim 1, wherein said holes cover about 3% to about 30% of the nominal surface area of said polymer substrate.

5. The construct of claim 1, wherein said holes are introduced in the 2D construct by laser ablation after first applying a photoresist-coating to said polymer substrate, and wherein said ablation is followed by removal of the photoresist after ablation.

6. The construct of claim 1, wherein the organometallic portion of said organometallic/phosphonate adduct is a metal alkoxide, metal oxide or mixed metal oxide-alkoxide.

7. The construct of claim 6, wherein said metal is zirconium or titanium.

8. The construct of claim 6, wherein the metal alkoxide is zirconium tetra(tert-butoxide).

9. The construct of claim 1, wherein the phosphonate ligand of said SAMP is a phosphonic acid covalently attached to the organometallic portion of said organometallic/phosphonate adduct, which phosphonic acid contains functionality adapted for cell binding.

10. The construct of claim 9, wherein said phosphonic acid adapted for cell binding contains one or more functional groups selected from the group consisting of polyol moieties, sugar alcohol moieties, hydroxyl functional groups, amino functional groups, carboxylic acid functional groups, carboxylate ester functional groups, phosphonic acid functional groups, phosphonate functional groups, ether functional groups, alkyne functional groups, azide functional groups and thiol functional groups.

11. The construct of claim 9, wherein said phosphonic acid adapted for cell binding is an α,ω-diphosphonic acid.

12. The construct of claim 11, wherein said α,ω-diphosphonic acid is 1,4-butane-diphosphonic acid or 1,12-dodecane-diphosphonic acid.

13. The construct of claim 1, further comprising a confluent cell layer attached to the coated surface of said polymer substrate, wherein the cells are spread around and between the holes, but do not block the holes, and are in alignment with the parallel cell-adhesive stripes.

14. The construct of claim 1, wherein the holes extend across 5% to about 30% of the nominal surface area of the polymer.

15. A method of preparing a 3-dimensional (3D) construct that supports cell attachment and alignment across three dimensions, comprising the steps of:

a) providing a biocompatible 2D laser-ablatable polymer substrate, optionally in sheet form;

b) coating said polymer substrate with a first photoresist to produce a photoresist-protected polymer substrate;

c) forming a pattern of single holes through said photoresist-protected substrate to produce a perforated protected substrate, wherein each of the elongated holes has a length dimension up to about 130 µm and a width dimension of about 20 to 40 µm, and wherein the elongated holes are arranged in rows such that holes in one row are offset from holes in a neighboring row so that holes in one row are staggered with those in the neighboring row in a direction of row progression;

d) removing the first photoresist from said perforated protected substrate to produce a perforated polymer substrate;

e) coating said perforated polymer substrate with a second photoresist coating pattern to pattern the perforated polymer substrate with a parallel-stripe, exposed polymer surface, wherein the pattern of the photoresist-covered perforations extends along the exposed polymer substrate in an orientation parallel to the stripe, exposed polymer surface;

f) forming a coating of a cell-adhesive organometallic/phosphonate adduct on said parallel stripes of exposed polymer substrate on the surface of said perforated polymer substrate, wherein said organometallic/phosphonate adduct comprises an organometallic layer covered with a phosphonate layer, and wherein the phosphonate layer comprises a self-assembled monolayer of a cell-adhesive phosphonate (SAMP) ligand;

g) removing said photoresist from said perforated polymer substrate to form a 2D construct coated with organometallic/phosphonate adduct stripes in micron-dimensioned continuous parallel lines, wherein said construct supports cell attachment and alignment across two dimensions; and h) stacking multiple said 2D constructs that support cell alignment and attachment across two dimensions to form a 3D construct, wherein said micron-dimensioned parallel stripe-patterned layer is dimensioned to (1) template attachment and proliferation of cells in register with the stripe pattern so that cell proliferation is aligned in the linear stripe direction and remains aligned over the entire surface and (2) allow the cells to grow to confluence, and wherein on each 2D construct, every cell is no more than about 200 μm from at least one elongated hole.

16. The method of claim 15, wherein the polymer of said biocompatible polymer substrate comprises polyetherether ketone (PEEK), optionally in sheet form.

17. The method of claim 15, wherein said holes are introduced by laser ablation.

18. The method of claim 15, further comprising the step of:

g1) incubating multiple 2D constructs of step g) with cells under conditions that form an ECM prior to stacking to form a 3D construct.

19. The method of claim 18, wherein said cells comprise NIH 3T3 fibroblasts.

20. A 3-dimensional (3D) construct that supports cell attachment and alignment along cell-adhesive continuous parallel stripe patterns, comprising stacked layers of a coated 2-dimensional (2D) construct that supports cell attachment and alignment across two dimensions, each 2D construct comprising:

a) a biocompatible laser-ablatable polymer substrate wherein the polymer surface is coated with a $ZrO_2$ interface that is directly reactive with a cell-adhesive phosphonate or phosphonic acid, said substrate having a pattern of elongated holes therethrough extending across the two-dimensional surface of the substrate, wherein each of the elongated holes has a length dimension up to about 130 μm and a width dimension of about 20 to 40 μm, and wherein the elongated holes are arranged in rows such that holes in one row are offset from holes in a neighboring row so that holes in one row are staggered with those in the neighboring row in a direction of row progression; and b) a patterned layer of an α,ω-diphosphonate or α,ω-diphosphonic acid directly attached to the surface of said substrate in a self-assembled monolayer of cell-adhesive phosphonate (SAMP) ligand in micron-dimensioned continuous parallel stripes, wherein the pattern of the holes extend along the parallel cell-adhesive stripes;

wherein the polymer substrate comprises polyacrylates, wherein said micron-dimensioned parallel stripe pattern is dimensioned to (1) template attachment and proliferation of cells in register with the stripe pattern so that cell proliferation is aligned in the linear stripe direction and remains aligned over the entire surface and (2) allow the cells to grow to confluence, and wherein on each 2D construct, every cell is no more than about 200 μm from at least one elongated hole; and further comprising a confluent cell layer attached to the coated surface of said polymer substrate, wherein the cells are spread around and between the holes, but do not block the holes, and are in alignment with the parallel cell-adhesive stripes.

21. A method of preparing a 3-dimensional (3D) construct that supports cell attachment and alignment across three dimensions, comprising the steps of:

a) providing a biocompatible 2D laser-ablatable polymer substrate that is coated with a $ZrO_2$ interface that is directly reactive with a cell-adhesive phosphonate, optionally in sheet form;

b) coating said polymer substrate with a first photoresist to produce a photoresist-protected polymer substrate;

c) forming a pattern of holes through said photoresist-protected substrate to produce a perforated protected substrate, wherein the holes are arranged in rows such that holes in one row are offset from holes in a neighboring row so that holes in one row are staggered with those in the neighboring row in a direction of row progression;

d) removing the first photoresist from said perforated protected substrate to produce a perforated polymer substrate;

e) coating said perforated polymer substrate with a second photoresist to pattern the perforated polymer substrate with a parallel-striped, exposed polymer surface, wherein the pattern of photoresist-covered perforations extends along the exposed polymer substrate in continuous lines in an orientation parallel to the striped, exposed polymer surface;

f) forming a coating of a cell-adhesive α,ω-diphosphonate or α,ω-diphosphonic acid directly on the parallel stripe-coated surface of said perforated polymer substrate;

g) removing said photoresist from said perforated polymer substrate to form a 2D construct coated with cell-adhesive α,ω-diphosphonate or α,ω-diphosphonic acid stripes directly attached to said polymer substrate in micron-dimensioned continuous parallel lines, wherein said construct supports cell attachment and alignment across two dimensions; and h) stacking multiple said 2D constructs that support cell alignment and attachment across two dimensions to form a 3D construct;

wherein the polymer substrate is selected from the group consisting of polyacrylates, polyamides and polyurethanes, and wherein said micron-dimensioned parallel stripe pattern is dimensioned to (1) template attachment and proliferation of cells in register with the stripe pattern so that cell proliferation is aligned in the linear stripe direction and remains aligned over the entire surface and (2) allow the cells to grow to confluence.

* * * * *